United States Patent
Buydts et al.

(10) Patent No.: US 9,561,189 B2
(45) Date of Patent: Feb. 7, 2017

(54) MULTI-COMPARTMENT DOSAGE FORM ARTICLES

(71) Applicant: Capsugel Belgium NV, Bornem (BE)

(72) Inventors: Hilde Buydts, Antwerp (BE); Stefaan Vanquickenborne, Rijmenam (BE)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 15/038,712

(22) PCT Filed: Oct. 23, 2014

(86) PCT No.: PCT/IB2014/002650
§ 371 (c)(1),
(2) Date: May 23, 2016

(87) PCT Pub. No.: WO2015/082983
PCT Pub. Date: Jun. 11, 2015

(65) Prior Publication Data
US 2016/0287522 A1 Oct. 6, 2016

Related U.S. Application Data

(60) Provisional application No. 61/911,070, filed on Dec. 3, 2013.

(30) Foreign Application Priority Data

Dec. 3, 2013 (EP) ..................... 13195563

(51) Int. Cl.
*A61K 9/48* (2006.01)
*A61K 9/00* (2006.01)
*A61J 3/07* (2006.01)

(52) U.S. Cl.
CPC .............. *A61K 9/4808* (2013.01); *A61J 3/072* (2013.01); *A61J 3/074* (2013.01); *A61K 9/0053* (2013.01);
(Continued)

(58) Field of Classification Search
None
See application file for complete search history.

(56) References Cited

U.S. PATENT DOCUMENTS

2005/0008690 A1* 1/2005 Miller .................... B29C 39/10
424/451

FOREIGN PATENT DOCUMENTS

EP 1 301 178 B1 1/2007
EP 2 211 820 B1 5/2012
(Continued)

OTHER PUBLICATIONS

European Search Report and Opinion issued Apr. 7, 2014, by the European Patent Office, for corresponding European Patent Application No. EP 13195563.5, filed Dec. 3, 2013, (EP Patent Publication No. EP2777802, published Sep. 17, 2014).
(Continued)

*Primary Examiner* — Robert A Wax
*Assistant Examiner* — Melissa Mercier
(74) *Attorney, Agent, or Firm* — Klarquist Sparkman, LLP (57) ABSTRACT

A dosage form article suitable for oral administration, comprising more than one compartments each delimited by a plurality of distinct segments selected from the group consisting of body parts, cap parts and combinations thereof. The dosage form article comprises: at least one first body part and at least one first cap part each comprising inner and outer surfaces, wherein the first body and cap parts are telescopically engageable; and at least one second body part, comprising inner and outer surfaces, being telescopically engageable with the at least one first body or cap parts or both. The at least one of the second body parts is arranged within the at least one first body part or cap part or both such that a distinct first compartment is formed between the outer (Continued)

surface of the second body part and the inner surface of the first body part or cap part or both.

20 Claims, 4 Drawing Sheets (52) U.S. Cl.
CPC ........... *A61K 9/0097* (2013.01); *A61K 9/4833* (2013.01); *A61J 2200/30* (2013.01); *A61J 2205/20* (2013.01); *A61J 2205/60* (2013.01)

(56) References Cited

FOREIGN PATENT DOCUMENTS

| WO | WO 2007/017725 A2 | 2/2007 |
| WO | WO 2009/138920 A1 | 11/2009 |

OTHER PUBLICATIONS

International Search Report and Written Opinion issued Apr. 16, 2015, by the European Patent Office for PCT Patent Application No. PCT/IB2014/002650, filed Oct. 23, 2014.

\* cited by examiner

MULTI-COMPARTMENT DOSAGE FORM ARTICLES

CROSS REFERENCE TO RELATED APPLICATIONS

This is the U.S. National Stage of International Application No. PCT/IB2014/002650, filed Oct. 23, 2014, which was published in English under PCT Article 21(2), which in turn claims the benefit of EP Patent Application No. 13195563.5, filed Dec. 3, 2013, and U.S. Provisional Application No. 61/911,070, filed Dec. 3, 2013, both of which are incorporated by reference herein in their entirety.

FIELD

The present disclosure relates to ingestible dosage form articles, preferably multi-part capsules, suitable for the delivery of one or more drugs and/or an ingestible signaling means. More particularly, the dosage form articles are suitable for ingestion by a subject, preferably the subject being selected from humans or animals.

Dosage form articles disclosed herein may also be used as part of diagnostic and therapeutic activities, in particular for recording adherence to a medicinal regimen.

BACKGROUND

Capsule technology continues to be subject to development and improvements. In its basic form, standard containers for pharmaceuticals or other powdered, granular or liquid substances (generally referred to as telescope-type or two-piece capsules) include a tubular-shaped and/or cylindrically-shaped first part, namely a cap part, which is closed on one end and open on the other opposite end. A tightly fitting second part of similar shape, namely the body part, is of smaller diameter than the cap part and is typically telescopically engaged therein to form the overall dosage form or two-piece capsule. Similar capsule technology may be used to generate multi-compartment capsules.

Multi-compartment dosage form articles of the above type are known, and are generally used for storing one or more incompatible components therein.

Some multi-compartment dosage forms are in the form of multiple two-piece capsules stored within one another. Generally this involves a larger two-piece capsule forming the outer shell of the dosage form and one or more smaller two-piece capsules therein storing different mediums therein. An example of this arrangement is described in EP1 301 178B1. Disadvantages of this arrangement include dislocation of the inner capsules with respect to the outer capsule which may result in damage of the content and/or capsules themselves during handling, overall size limitations of the dosage form, and the need for complex filling processes.

Other multi-compartment dosage forms, such as described in EP2 211 820B1, are in the form of two-piece capsules with a main cap and a main body being joined to form a first compartment and a further body joined to the outer surface of the aforementioned main body to form a second compartment. Disadvantages of this arrangement include increased overall volume size of the dosage form (particularly overall length of the same) which may be undesirable for swallowability, risk of premature disengagement of the further body from the main body with subsequent spill of the content during handling, as well as requiring complex filling processes in order to fill and assemble the final product.

Therefore there still remains a need for a dosage form article that overcomes the problems of the prior art and in particular allows for a multi-compartment capsule that minimizes overall size of the dosage form, and/or improved resistance during handling, and/or simplifies assembly and filling processes of the same.

SUMMARY

A first aspect of the present disclosure relates to a dosage form article suitable for oral administration, comprising more than one compartments each delimited by a plurality of distinct segments of the dosage form article, the distinct segments being selected from the group consisting of body parts, cap parts and combinations thereof, wherein the dosage form article comprises: at least one first body part and at least one first cap part each comprising inner and outer surfaces, wherein the first body and cap parts are telescopically engageable; and at least one second body part, comprising inner and outer surfaces, being telescopically engageable with the at least one first body or cap parts or both. The at least one of the second body parts is arranged within the at least one first body part or cap part (103) or both such that a distinct first compartment is formed between the outer surface of the second body part and the inner surface of the first body part or cap part (103) or both.

A further aspect of the present disclosure relates to methods of filling the same.

BRIEF DESCRIPTION OF THE DRAWINGS

FIGS. 4 (A and B) is an illustration of the operation of a method according to an aspect of the disclosure.

DETAILED DESCRIPTION

By the term "a" and/or "an" when describing a particular element, it is intended "at least one" of that particular element.

By the term "medicament", it is intended a "drug" or the like comprising one or more compounds providing one or more curative benefits to a subject, the terms "medicament" and "drug" may be used interchangeably herein.

By the term "hard shell" or "hard capsule shell", it is intended a shell that is deformable, but which returns to its un-deformed shape upon the removal of a deforming force. Typically such shells comprise, for example, less than 25%, preferably less than 20%, more preferably from 0% to 14%, even more preferably from greater than 0% to less than 14%, water by weight.

By the term "wholly incorporated", it is intended that the element referred to is fully contained within the dosage form article such that no surfaces of said element are directly in contact with any portion of a volume external to the dosage form article. Such generally being formed when the dosage form article is in assembled state.

By the term "compartment", it is intended as a definite volume for storing a drug, or signaling means therein, each volume being formed and delimited by multiple parts (i.e. a plurality of distinct segments) when connected to each other.

By the term "multiple parts" or "plurality of distinct segments", it is intended the portions making up the dosage form article which, when connected, form one or more compartments. Such portions are separate components and typically comprise, preferably consist of, cap part(s), body part(s), and combinations thereof.

By the term "arranged within", it is intended that, for example, at least 70%, preferably at least 80%, more preferably at least 90%, even more preferably more than 95%, most preferably 100%, of the surface area of the element referred to is located inside another element referred to.

Various embodiments will now be described to provide an overall understanding of the principles of the structure, function, manufacture, and use of dosage form articles and methods disclosed herein. One or more examples of these embodiments are illustrated in the accompanying figures. Those of ordinary skill in the art will immediately understand that features described or illustrated in connection with one example embodiment can be combined with the features of other example embodiments without generalization from the present disclosure.

Dosage Form Articles

Figure 1:
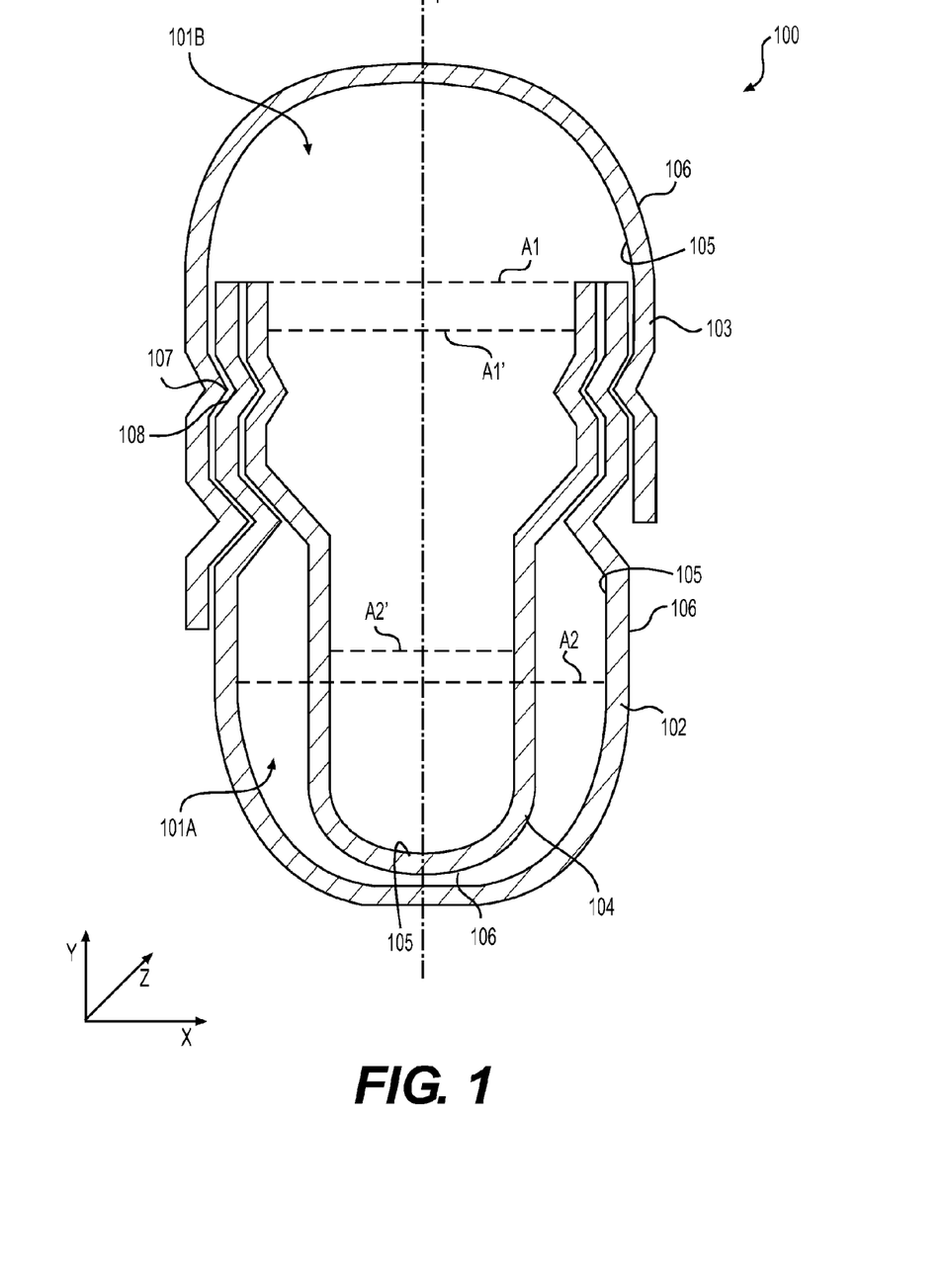
FIG. 1 is an illustration of a cross-sectional view of a dosage form article according to one aspect of the disclosure.
Figure 2:
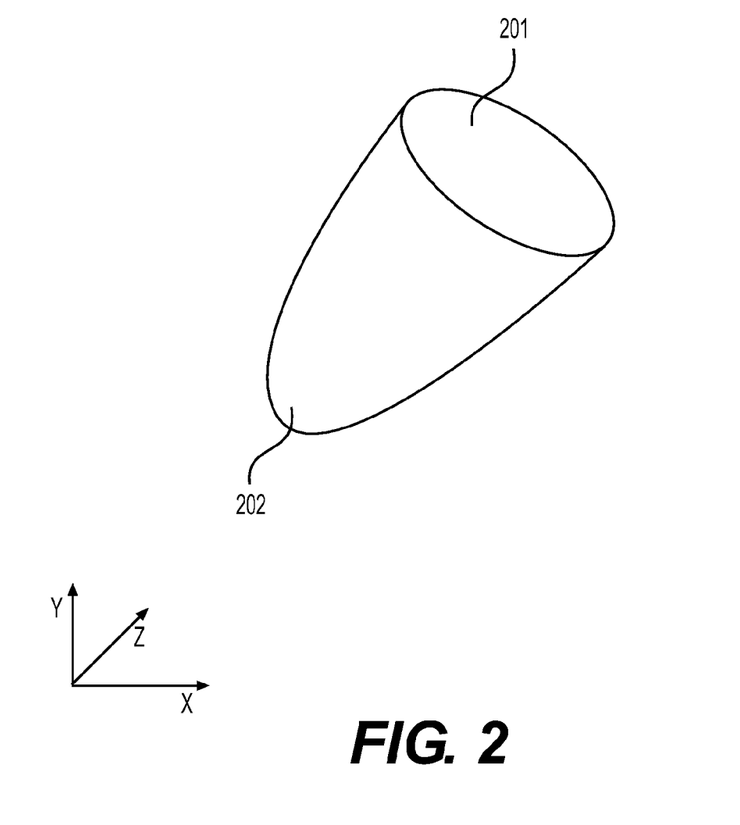
FIG. 2 is a perspective representation of a portion of the dosage form article according to one aspect of the disclosure.

Referring to FIGS. 1 and 2, the disclosure herein relates to a dosage form article 100 suitable for oral administration, comprising more than one compartments 101a, 101b each delimited by a plurality of distinct segments 102, 103, 104 of the dosage form article 100, said distinct segments being selected from the group consisting of body parts 102, 104, cap parts 103 and combinations thereof, wherein said dosage form article 100 comprises: at least one first body part 102 and at least one first cap part 103 each comprising inner 105 and outer 106 surfaces, wherein said first body part 102 is telescopically engageable with said cap part 103, preferably such that at least a portion of the outer surface of the first body part abuts a respective portion of the inner surface of the first cap part; and at least one second body part 104 (or second cap part, since it is understood herein that a second cap part can equally and/or alternatively be used), comprising inner 105 and outer 106 surfaces, being telescopically engageable with said at least one first body 102 or cap 103 parts or both, wherein at least one of the second body parts 104 is arranged within said at least one first body part 102 or cap part 103 or both such that a distinct first compartment 101a is formed, preferably only, between the outer surface 106 of said second body part 104 and the inner surface 105 of said first body part or cap part 103 or both. An advantage of this configuration is simplified filling operation of the multi-chambers as well as improved flexibility since several mediums may be pre-filled and closed in the body-to-body compartment(s) to then be further filled and finally closed to form the end dosage form at a later stage in the process. The latter enables, for example, the pre-filling of certain mediums by a capsule manufacturer and filling certain other mediums (post-pre-filling) by a drug developer without having to substantially modify the filling processes. Another advantage includes overall volume maximization which in turn aids in reducing the overall size of the dosage form compared to known multi-compartment dosage forms. Moreover, the overall exterior aesthetic impression of the dosage form (in terms of outer shape) does not change versus standard capsules thus providing benefits in terms of consumer acceptance.

The second body part 104 may be arranged within the first body part 102 such that, once the first cap part 103 is telescopically connected (or engaged) with the first body part 102, second body part 104 or both, the second body part 104 separates a volume formed by the first body and cap parts 103, 103 into at least two distinct compartments. Further compaction and ease of filling is achieved with such arrangement.

The first body part 102 may be arranged to telescopically engage with the first cap part 103 such that at least a portion of the inner surface 105 of the first cap part 103 abuts at least a portion of the outer surface 106 of the first body part 102, and wherein the at least second body part 104 is arranged to telescopically engage with the first body part 102 such that at least a portion of the inner surface 105 of the first body part 102 abuts at least a portion of the outer surface 106 of the second body part 104. Such portions may be proximal to an open end of respective body and cap parts.

In an embodiment, the dissolution properties of the first body part is different from the dissolution properties of the second body part and/or first cap part, preferably wherein the second body part and/or first cap part dissolves at a faster or slower rate than the first body part. This may bring advantages such as more accurate sequential release of the contents of respective compartments.

Preferably, the second body part 104 is arranged such that a second compartment 101b is formed between the inner surface 105 of at least one of the second body parts 104 and the inner surface 105 of the first cap part 103.

Each body and cap parts 102, 103, 104 may comprise an open end 201 and a closed end 202, preferably wherein the open end is the only open end such that a semi-enclosed volume substantially tubular in shape is formed, wherein the first and at least second body parts 102, 104 comprise a first area A1, A1' proximal to the open end 201 and a second area A2, A2' proximal to the closed end 202 and distal from said open end 201. The first and second areas are generally cross-sectional areas over a plane perpendicular to the Y-axis. The second area is typically less than or equal to the first area. It is preferred that the area ratio A1/A2 of the first body part 102 is less than the area ratio A1'/A2' of the second body part 104. This has the advantage of providing multiple compartments whilst further minimizing overall size of the dosage form and ensuring overall volume maximization. Moreover, it guarantees a secure fit allowing for simple location of the content in the first compartment in the dosage form article as well as ensuring ease of assembly and filling operations of each respective compartment. The area ratio A1'/A2' of the second body part 104 may be, for example, at least 1.1, preferably at least 1.2, more preferably at least 1.3, preferably from 1.2 to 5, more preferably from 1.4 to 2.5, times greater than the area ratio A1/A2 of the first body part 102. Such ratios may further maximize volume of the compartments suitable for filling whilst minimizing overall size of the dosage form, whilst also being manufacturable across a range of capsule sizes.

The first and second areas may be substantially parallel to each other and distal from one another, preferably along a vertical plane parallel to a centerline (i.e. Y-axis) of the dosage form article. The distance between the first and second area may be, for example, from 40% to 75%, preferably from 45% to 70%, more preferably from 50% to 70%, even more preferably from 60% to 70%, of the total length of a body part (first or second body parts).

In an embodiment, the length (in a direction parallel to the y-axis) of the first body part is greater than the length of the second body part. Typically, the length ratio (length of the second body part divided by the length of the first body part) may be, for example, from greater than 0 to 0.95, preferably from greater than 0 to less than 0.95, more preferably from greater than 0 to less than 0.90, more preferably from greater than 0 to less than 0.80, more preferably from greater than 0 to less than 0.70, even more preferably from greater than 0 to less than 0.60. This embodiment has the advantage of allowing additional filling volume between surfaces of the first and second body caps proximal to respective closed ends.

Typically, each body and/or cap parts are tapered such that the diameter of the closed end is smaller than the diameter of the open end of each body and/or cap parts. Preferably, the second body part comprises more than one tapers arranged such that at least a first taper is proximal to the open end and at least a second taper is proximal to the closed end, the first taper may extend from a circumference of the body and/or cap parts (e.g. along the outer surface of the body/cap parts) towards a centerline (Y-axis). The first taper may be less than the second taper. The advantage of this configuration is to achieve body parts having optimal shapes for being locked into each other and allowing sufficient spacing therebetween for generating volume efficient multi-compartment dosage form articles. It also ensures that the diameter of a lower portion of the cap/body part is substantially less than the diameter of an upper portion of the cap/body part in order to maximize available volume for the compartments whilst minimizing overall size of the dosage form. It also permits to securely lock the second body/cap parts within the first body/cap parts about respective positions proximal to the upper portion.

The second body parts may have an upper portion and a lower portion adjacently located to respective first body part upper and lower portions (when in assembled state), the ratio of the diameters of the upper and lower portions (i.e. diameter of upper portion over diameter of lower portion) of the second body part is greater than the respective upper and lower portion ratio of the first body part.

Each body and cap parts 102, 103, 104 may comprise one or more protruding locking means 107 and/or one or more recessed locking means 108, the protruding locking means 107 capable of mechanically engaging with the recessed locking means 108 to provide a locking force joining the body and/or cap parts 102, 103, 104 together, preferably the protruding locking means 107 is in the form of a locking ring protruding along a plane perpendicular to a Y-axis in a direction from the outer surface 106 to the inner surface 105 and the recessed locking means 108 is in the form of a recessed ring, the recess starting from the outer surface 106 and extending towards the inner surface 105. Advantageously such arrangement allows to securely mechanically engage respective portions of the body and cap parts to generate respective compartments. In an embodiment, at least a portion of the second body is engaged onto at least a portion of the inner surface of the first body part so that the second body sits within the first body part.

The at least first and second body parts 102, 104 each may comprise one or more protruding locking means 107 arranged in series with one or more recessed locking means 108 along an axis perpendicular to the Y-axis. This has the advantage of enabling effective body-to-body and/or cap-to-cap and/or body-to-cap engagement without the need of generating separate (or multiple additional) protruding and recessed regions.

In an embodiment at least one of the protruding locking means of the first body part is arranged such that it provides a shoulder for a complementary portion of the second body part to rest on. This has the advantage of providing for good and secure location of the second body part within the first body part.

When a signaling means is filled in the first compartment 101a, at least one of the protruding locking means of the first body part may be arranged such that it provides a shoulder restricting movement of the signaling means along the y-axis.

The dosage form article may further comprise one or more spray rings formed as an annular recess on the first body part and positioned distal from at least one of the recessed locking means in a direction parallel to the y-axis and proximal to the apex of the first cap part when the two are fully telescopically connected, said apex being adjacent to the open end of said first cap part. The spray ring is typically arranged such that it is positioned below said apex when the first body and first cap are telescopically connected such that the apex, typically annular in form running substantially parallel to the annular spray ring, does not obstruct a gap formed between said spray ring and said apex to allow a sealing liquid to be sprayed therebetween. The advantage of this configuration is to further ease wicking of the sealing liquid through the spacing between inner surface of the first cap part and outer surface of the first body part by better directing said sealing liquid to said spacing when sprayed. It further ensures that any amount of sealing liquid pushed out during drying (due to pressure build-up within the dosage form article) is collected within the gap formed between the spray ring and the apex.

At least a first compartment 101a may be, preferably only, delimited by the first body part 102 and one of the at least second body parts 104, preferably by the inner surface 105 of the first body part 102 and the outer surface 106 of the second body part 104, and wherein at least a second compartment 101b may be, preferable only, delimited by the first cap part 103 and one of the at least one second body parts 104, preferably by the inner surface 105 of the first cap part 103 and the inner surface 105 of the second body part 104.

It is understood that dosage form articles herein may comprise a plurality of second body parts, typically stored within one another (e.g. a first second body part storing therein a second/further second body part, said second/further second body part storing therein a third/further second body part etc.). Preferably, one or more further second body parts may be comprised, each arranged within at least one second body part such that at least one further compartment is formed between an outer surface of the further second body part and the inner surface of the at least one second body part 104. This has the advantage of enabling incorporation of several different mediums therein which may be in the same or different phases and/or be incompatible if kept in the same compartment.

The first compartment 101a may comprise a first drug or a signaling means therein and another of the compartments may comprise a second (or further) drug therein. The first and second drug may be in solid or liquid form, preferably the first and second drug are in different phases.

The first body part 102 may be translucent such that the second body part 104 and/or the first compartment 101a can be seen through the dosage form article, preferably wherein the second body part 104 is opaque. This may be particularly useful if a signaling means is stored in the first compartment which requires a subject to visually inspect it.

The first compartment 101a may comprise a liquid and the first body part 102 may be translucent such that the liquid can be seen through the dosage form article. This may be advantageous to provide different aesthetic effects to improve subject acceptance of the dosage form article. Also, when the liquid is a signaling means in the form of indicia, a subject may process the visual signal accordingly to determine an action.

In an embodiment, a liquid seal is comprised between the outer surface 106 of the second body part 104 and the inner surface 105 of the first body part and/or between the outer surface 106 of the first body part 102 and the inner surface 105 of the first cap part 103, preferably wherein the liquid seal is formed by allowing a sealing liquid to enter a spacing between said outer and inner surfaces 106, 105, typically by capillary action or pressure difference between pressure within the dosage form and outside the dosage form, followed by drying. Preferably, the second body part 104 is connected to both first body part 102 and first cap part 103 and a liquid seal is comprised only between the outer surface 106 of the second body part 104 and the inner surface 105 of the first body part. This latter arrangement has the advantage that a single seal is needed whilst ensuring liquid tight multi-compartments. Preferably, the liquid seal is located proximal to the respective open ends of abutting cap and/or body and/or body parts. The seal has the further advantage of improving the tamper resistance of the dosage form such that it may not be opened post-treatment without visibly damaging the dosage form.

The first body part 102, preferably when the first compartment 101a is used for storing a signaling means, may comprise one or more openings typically proximal to the closed end of the body part, said openings may be, for example, from 500 μm to 2000 μm, preferably from 800 μm to 1500 μm, in diameter. This has the advantage to allow fluids to enter the compartment, particularly when storing a signaling means therein the latter may be conveniently activated (e.g. upon reaching a predetermined pH in reaction to in-body acids) or may allow certain pre-subministration parameters to be recorded (e.g. humidity). The holes may also aid in controlling dissolution for targeted opening of the respective compartments within the dosage form article.

In an embodiment the dosage forms described herein may comprise a plurality of second compartments, stored within one another and each may have different dissolution properties. This has the advantage that multiple different drugs and/or multiple different signaling means may be stored within a single dosage form article, and may be released at different predetermined positions in the gastrointestinal tract.

In an embodiment, the first body and cap parts and the second body parts are prevented from movement once engaged, preferably via a snap fit, such that no said parts may dislocate during handling of the dosage form. Such arrangement may introduce benefits such as reduced risk of damaging the contents (e.g. signaling means when used) during handling as well as accurate location of components within the dosage form, particularly in assembly and filling processes.

In an embodiment the dosage form articles herein are multi-piece capsules comprising a plurality of capsule shells. The capsule shells may each comprise locking features to mechanically lock with one or more other capsule shells. Said features may comprise a combination of protrusions and recesses of complementary shape such that when interposed lock the capsule shells together.

The dosage form articles herein may be made of, or consist of, an ingestible material comprising materials selected from the group consisting of gelatin, one or more polysaccharides, preferably pullulan; nonionic hydrogels, preferably cellulose such as hydroxypropyl methylcellulose (HPMC); and mixtures thereof. Most preferred materials being gelatin and/or hydroxypropyl methylcellulose (HPMC). Dosage form articles herein may be non-injection molded, and preferably made via a dip molding process. The latter ensures high production speeds and cost effectiveness. Other materials may also be used, as will be recognized by one skilled in the art, including cellulose ethers, such as starches (e.g. waxy maize starch, tapioca dextrin, and derivatives thereof), carrageenan, and polymers or copolymers of (meth)acrylic acids and derivatives thereof.

Typically, the cap and body parts may be substantially tubular in shape and each comprise a single opening. The cap and/or body parts described herein may be hard capsule shells.

Signaling Means

One or more signaling means may be stored within dosage form articles described herein.

Figure 3:
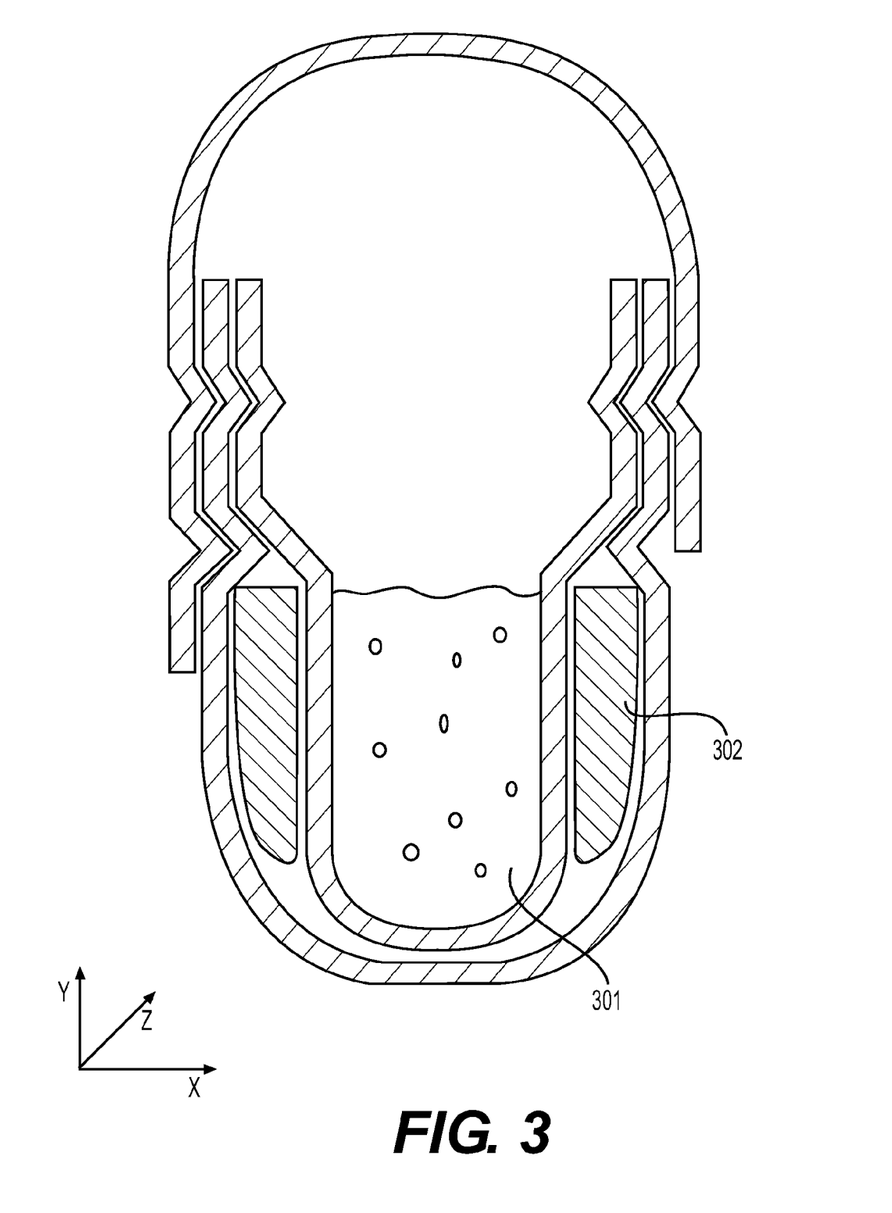
FIG. 3 is an illustration of a cross-sectional view of a dosage form article according to one aspect of the disclosure.

The signaling means 302 may be selected from the group consisting of an ingestible passive micro-electronic system, preferably comprising a radio frequency emitter; ingestible indicia, preferably indicia that undergoes a visual transformation, such as color change, when exposed to predetermined physical changes, such as an increase in temperature over a predetermined amount or a change in color with time (or aging), or a barcode-like readable medium; and combinations thereof.

In one embodiment the signaling means is an ingestible passive micro-electronic system. The passive micro-electronic system may comprise an ingestible radio frequency emitter and a power source. The radio frequency emitter may comprise one or more antennas and preferably a processing unit.

The power source may use power conditioning to extract energy from electromagnetic fields and/or internal electrical sources generated by internal biological electrochemical interactions within the subject body. The power source may be arranged to use electrochemical reactions between internal gastric acid, oxidizing and reduction electrodes to activate the passive micro-electronic system and provide one or more signal bursts after reaching a predetermined position in the gastrointestinal tract (for example by reacting at a predetermined pH level).

The power source may, alternatively or in combination with the above described power conditioning, comprise a micro battery storing sufficient energy to power one or more signal bursts when activated.

The antenna may be designed to fold within a compartment of dosage form articles herein and arranged to deploy so as to expand its surface area versus the folded state but without exceeding the maximum surface area of the dosage form article. The advantage of this embodiment is the reduced risk of the antenna wrapping around part of the compartment storing the drug, when the antenna is deployed, which may otherwise delay its release from the desired predetermined position.

The dosage form article and/or the antenna may be arranged to deploy said antenna at a predetermined position in the gastrointestinal tract, the antenna may comprise one or more bio-compatible materials and may be free of protective coatings.

The processing unit may be in electrical communication with the antenna and arranged to provide a signal burst once activated by the power source, said signal burst then being transmitted by the antenna through the body of a subject to be captured and/or read by a receiver.

The radiofrequency emitter, typically including the antenna and processing unit, and the power source may be integrated into a single device to form the passive micro-electronic system. This has the advantage of easily locating all functional components within the dedicated compartment of the dosage form articles described herein, thus simplifying the assembly.

The ingestible passive micro-electronic system may further comprise one or more micro sensors preferably temperature and/or humidity sensors, arranged to record exposed temperature and humidity and send the information to the processing unit. In this embodiment the processing unit comprises a memory wherein maximum temperature and humidity parameters are stored, the processing unit further comprising a microprocessor for comparing the temperatures/humidity recorded by the sensor with the predetermined temperature/humidity parameter stored in the memory and arranged such that if the recorded measurement exceeds the predetermined parameter, a signal burst is generated. The signal burst may be delayed up to when a trigger is provided, for example by a subject scanning the dosage form article with a respective scanner and/or receiver. The advantage of this embodiment is that the subject may scan the dosage form article containing the signaling means therein and the signaling means will provide a signal to the receiver as to whether the parameters stored in the memory have been exceeded, i.e. the subject will know whether the dosage form has been exposed to e.g. excessively high temperatures which renders ingestion of the medicament unsafe.

It is understood herein that the sensor described herein above may take several forms and should not be limited to the above example. For example, the sensor may comprise a timer, the timer may be activated upon assembly of the dosage form or upon filling of the dosage form with a drug. The microprocessor may be arranged to compare a preset time parameter stored in the memory with the reading of the timer, and once the reading of the timer exceeds the preset time parameter the processor is arranged to provide a signal burst. Like in the above example, the signal burst may be delayed up to when a trigger is provided, for example by a subject scanning the dosage form article with a respective scanner and/or receiver. In this case the advantage is that the subject may identify whether a medicament has expired by simply scanning the dosage form article containing the signaling means. This is particularly useful as one may identify whether safe to ingest a medicament directly from the dosage form without consulting the date on the box (e.g. in case misplaced, or label damaged/faded). The scanner/receiver may be arranged to provide a combinations of triggers to the user, for example visual and audio to instruct the subject whether a medicament has expired (or exposed to high temperatures etc.).

Alternatively or additionally, the signaling means may be ingestible indicia capable of changing color following a predetermined change in conditions or aging. The indicia may comprise florescent or phosphorescent agents. More preferably, the signaling means comprises one or more indicating bodies, wherein the indicating bodies comprise one or more temperature sensitive or age sensitive materials, said materials typically capable of undergoing a chemical reaction when either exposed to a temperature above a predetermined maximum level or aging beyond a predetermined maximum time or both.

Temperature sensitive color changing materials are also known as thermochromic (or thermochromatic), and are typically selected from the group consisting of thermochromatic liquid crystals, leuco dyes, and mixtures thereof. Leuco dyes may be selected from one or more spirolactones, fluorans, spiropyrans, and mixtures thereof. Temperature sensitive color changing materials may undergo a permanent/irreversible color change once exposed to a temperature above a predetermined value.

In a preferred embodiment the indicating bodies may be in the form of microcapsules containing the thermochromatic materials therein. The microcapsules may be made of a material which is non-digestible and remains intact throughout the gastrointestinal tract until excreted as solid waste. The microcapsules may be, for example, from 200 µm to 3000 µm, preferably from 500 µm to 2000 µm, more preferable from 1000 µm to 2000 µm, in diameter.

Alternatively or additionally, the signaling means may be in the form of a barcode-like readable medium, preferably a barcode (e.g. one-dimensional or two-dimensional barcode). The barcode-like medium may store information such as the date of expiry of the drug stored in the dosage form article, the identity of the drug stored in the dosage form article etc. The subject may then be able to scan the barcode-like readable medium through the relevant portion of the dosage form article via the respective scanner and be provided with an indication of whether still safe to ingest (e.g. expiry date still not reached) and/or information as to the interval the scanned medicament should be taken. In an embodiment, the scanner may comprise a memory wherein information scanned is stored, and a programmable processor capable of comparing the information stored in the memory with the new information received when scanning a dosage form article and provide a signal in case the detected drug is incompatible with a previously taken drug, or whether the time interval from the previously taken drug does not meet predetermined criteria. This is particularly advantageous for subjects who are taking multiple medicaments (for one or more treatments) and is important to time the administration, as well as to aid the subject to stay within the administration regimen provided by the prescriber. In an embodiment, only the prescriber may input the required parameters in the scanner to program the processor, the scanner having an access key preventing the subject to modify the program of the programmable processor.

Drug/Medicament

Dosage form articles described herein may comprise one or more drugs 301. Drugs suitable for use in the dosage forms described herein may take any form and be for any treatment of a human or animal subject. This includes not only pharmaceutical compounds but also dietary supplements such as vitamins, minerals and the like.

The drug may be in a state selected from solid or liquid, at room temperature and atmospheric pressure, and comprises one or more active compounds. The physical state of said drug is typically wholly dependent on the needs for a given application. When the drug is in solid state the drug may be powder-like or caplet-like (i.e. tablet-like). In an embodiment, the drug is in the form of a caplet or tablet typically having a first and second end. The caplet or tablet may be further coated, alternatively or additionally, at least one, preferably both, first and second ends of the caplet or tablet may be coated with capsule shells. The capsule shells may be gelatin comprising or hydroxypropyl methylcellulose (HPMC) comprising shells. By "capsule shells" it is herein intended at least portions of body or cap parts of hard capsule shells cut to size such to fit and insert over the outer surface of the caplet or tablet to provide a tight fit when joined. The capsule shells may be further treated following insertion over the caplet or tablet such to firmly adhere thereto, preferably by shrinking.

Suitable compounds for delivery according to the disclosure include, but are not limited to, powder, liquid, and/or pellet forms of the following:

a) pharmaceuticals (also called pharmaceutical actives) such as betamethasone, thioctic acid, sotalol, salbutamol, norfenefrine, silymahn, dihydroergotamine, buflomedil, etofibrate, indomethacin, oxazepam, acetyldigitoxins, piroxicam, halopehdol, isosorbide mononitrate, amithptyline, diclofenac, nifedipine, verapamil, pyritinol, nitrendipine, doxy-cycline, bromhexine, methylprednisolone, clonidine, fenofibrate, allopurinol, pirenzepine, levothyroxine, tamoxifen, metildigoxin, o-(B-hydroxyethyl)-rutoside, propicillin, aciclovirmononitrate, paracetamolol, naftidrofuryl, pentoxifylline, propafenone, acebutolol, 1-thyroxin, tramadol, bromocriptine, loperamide, ketofinen, fenoterol, ca-dobesilate, propranolol, minocycline, nicergoline, ambroxol, metoprolol, B-sitosterin, enalaprilhydro-genmaleate, bezafibrate, isosorbide dinitrate, gallopamil, xantinolnicotinate, digitoxin, flunitrazepam, bencyclane, depanthenol, pindolol, lorazepam, diltiazem, piracetam, phenoxymethylpenicillin, furosemide, bromazepam, flunarizine, erythromycin, metoclo-pramide, acemetacin, ranitidine, biperiden, metamizol, doxepin, dipotassiumchloraze-pat, tetrazepam, estramustinephosphate, terbutaline, captopril, maprotiline, prazosin, atenolol, glibenclamid, cefaclor, etilefrin, cimetidine, theophylline, hydromorphone, ibu-profen, primidone, clobazam, oxaceprol, medroxyprogesterone, flecainide, Mg-pyhdoxal-5-phosphateglutaminate, hymechromone, etofyllineclofibrate, vincamine, cin-narizine, diazepam, ketoprofen, flupentixol, molsidomine, glibornuhde, dimethindene, melperone, soquinolol, dihydrocodeine, clomethiazole, clemastine, glisoxepid, kallidino-genase, oxyfedhne, baclofen, carboxymethylcystsin, thioredoxin, betahistine, 1-tryptophan, myrtol, bromelain, prenylamine, salazosulfapyridine, astemizole, sulpiride, benzerazid, dibenzepin, acetylsalicylic acid, miconazole, nystatin, ketoconazole, sodium picosulfate, colestyramate, gemfibrozil, rifampin, fluocortolone, mexiletine, amoxicillin, terfenadine, mucopolysaccharidpolysulfuric acid, triazolam, mianserin, tiaprofensaure, ameziniummethylsulfate, mefloquine, probucol, quinidine, carbamazepine, Mg-1-aspartate, penbutolol, piretanide, amitriptyline, caproteron, sodium valproinate, mebeverine, bisacodyl, 5-amino-salicyclic acid, dihydralazine, magaldrate, phenprocou-mon, amantadine, naproxen, carteolol, famotidine, methyldopa, auranofine, estriol, nadolol, levomepromazine, doxorubicin, medofenoxat, azathioprine, flutamide, norfloxacin, fendiline, prajmaliumbitartrate, aescin acromycin, anipamil, benzocaine, [beta]-carotene, cloramphenicol, chlorodiazepoxid, chlormadinoneacetate, chlorothiazide, cin-narizine, clonazepam, codeine, dexamethasone, dicumarol, digoxin, drotaverine, grami-cidine, griseofulvin, hexobarbital hydrochlorothiazide, hydrocortisone, hydroflumethiazide, ketoprofen, lonetil, medazepam, mefruside, methandrostenolone, sulfaperine, nalidixic acid, nitrazepam, nitrofurantoin, estradiol, papaverine, phenacetin, phenobarbi-tal, phenylbutazone, phenytoin, prednisone, reserpine, spironolactine, streptomycin, sul-famethizole, sulfamethazine, sulfamethoxazole, sulfamethoxydiazinon, sulfathiazole, sulfisoxazole, testosterone, tolazamide, tolbutamide, trimethoprim, tyrothricin, antacids, reflux suppressants, antiflatulents, antidopaminergics, proton pump inhibitors, H2-receptor antagonists, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, ACE inhibitors, angiotensin receptor blockers, alpha blockers, anticoagulants, heparin, antiplatelet drugs, fibrinolytic, anti-hemophilic factor, haemostatic drugs, hypolipidaemic agents, statins, hypnotics, anaesthetics, antipsychotics, antidepressants (including tricyclic antidepressants, monoamine oxidase inhibitors, lithium salts, selective serotonin reuptake inhibitors), anti-emetics, anticonvulsants, an-tiepileptics, anxiolytics, barbiturates, movement disorder drugs, stimulants (including amphetamines), benzodiazepine, cyclopyrrolone, dopamine antagonists, antihistamines, cholinergics, anticholinergics, emetics, cannabinoids, 5-HT antagonists, analgesics, muscle relaxants, antibiotics, sulfa drugs, aminoglycosides, fluoroquinolones, bronchodilators, NSAIDs, anti-allergy drugs, antitussives, mucolytics, decongestants, corticosteroids, beta-receptor antagonists, anticholinergics, steroids, androgens, antian-drogens, gonadotropin, corticosteroids, growth hormones, insulin, antidiabetic drugs (including sulfonylurea, biguanide/metformin, and thiazolidinedione), thyroid hormones, antithyroid drugs, calcitonin, diphosphonate, vasopressin analogs, contraceptives, follicle stimulating hormone, luteinising hormone, gonadotropin release inhibitor, progestogen, dopamine agonists, oestrogen, prostaglandin, gonadorelin, clomiphene, tamoxifen, di-ethylstilbestrol, antimalarials, anthelmintics, amoebicides, antivirals, antiprotozoals, vaccines, immunoglobulin, immunosuppressants, interferon, monoclonal antibodies, and mixtures thereof;

b) vitamins, e.g., fat-soluble vitamins such as vitamins A, D, E, and K, and water soluble vitamins such as vitamin C, biotin, folate, niacin, pantothenic acid, riboflavin, thiamin, vitamin B6, vitamin B12, and mixtures thereof;

c) minerals, such as calcium, chromium, copper, fluoride, iodine, iron, magnesium, manganese, molybdenum, phosphorus, potassium, selenium, sodium (including sodium chloride), zinc, and mixtures thereof;

d) dietary supplements such as herbs or other botanicals, amino acids, and substances such as enzymes, organ tissues, glandulars, and metabolites, as well as concentrates, metabolites, constituents, extracts of dietary ingredients, and mixtures thereof;

e) homoeopathic ingredients such as those listed in the Homeopathic Pharmacopoeia of the United States Revision Service (HPRS), and mixtures thereof. It must be recognized, of course, that the HPRS is periodically updated and that the present invention includes homeopathic ingredients that may be added to the HPRS; and mixtures in any combination of the foregoing.

It is also contemplated that mixtures of compatible ingredients can be included in one compartment and other ingredients which are not compatible with the contents of one compartment or other ingredients which are desirably placed in another compartment can also be used as part of the present disclosure. For example, a first compound may be included in one compartment in a powdered dosage form while a second compound may be included in a second compartment in a liquid dosage form. The ability to administer different dosage forms in a single dosage unit avoids not only any incompatibilities between the compounds and/ or their dosage forms, but also the expense often incurred in reformulating one or the other compound into a compatible dosage form.

Methods

Dosage form articles as described herein may be used in a number of methods and applications, the below passages will describe some of the methods in which dosage form articles as described may be particularly useful.

The disclosure herein encompasses a method of assembly, of dosage form articles described herein, typically comprising the steps of: providing a first body part; optionally filling the first body part with a first medium, preferably by inserting said first medium typically comprising or consisting of a signaling means within the first body part or by filling said first medium typically comprising or consisting of a drug in solid or liquid state therein; providing a second body part; optionally filling said second body part preferably with a drug in solid or liquid state; inserting said second body part within said first body part and joining a portion of the second body part to the first body part such to connect the two together and form a first compartment therebetween; and joining a first cap part to said first body part such to connect the two together with the second body part therein forming a second compartment between said first cap part and said second body part.

Typically, a method of filling a dosage form article 100 comprises the, preferably sequential, steps of: providing a first body part 102; filling said first body part 102 with a first medium; inserting a second body part 104 into said first body part 102 such that a first compartment 101a is formed for storing said first medium and optionally joining said second body part 104 to said first body part 102; filling said second body part 104 with a second medium; optionally, connecting a first cap part 103 with said first body part 102 or second body part 104 or both, such that a second compartment 101b is formed for storing said second medium; and optionally, wherein the first medium is selected from a drug in solid or liquid state, or a signaling means, and the second medium is selected from a drug in solid or liquid state. This may be repeated for any number of further second body parts depending on the number of compartments desired. It is further understood that the above steps may be performed at any time and by the same or different entities, preferably wherein the overall steps are performed in sequence. The first body part and second body part may be locked with the first medium therein prior to further filling and complete assembly of the dosage form, and the first cap part may be pre-locked to the first body part prior to filling with the second medium. This has the advantage that filling of the second medium and final/full assembly of the end dosage form may be completed by the same or different entity at a later stage in production without the need of drastically changing filling process equipment.

Particularly when a signaling means is incorporated in dosage form articles herein, the following advantageous methods may be performed.

A method of measuring compliance with a medical regimen may comprise the steps of: administering to a subject a dosage form; providing a receiver for detecting a signal produced by the signaling means preferably when the dosage form reaches a predetermined position in the gastrointestinal tract of the subject; and optionally recording administration parameters via a recording device which may be in electrical communication with said receiver, said administration parameters preferably selected from the group consisting of date, time, and combinations thereof. Such method has the advantage of ensuring complete traceability and adherence to a medical regimen. By digitally logging information of when a given dosage form or array of dosage forms are ingested, such information may be easily and reliably extracted for a number of further studies as well as ensuring compliance with a medical regimen.

Further or as an alternative to the above method, a method for determining whether it is safe to ingest a medicament may comprise the steps of: providing a dosage form article; comparing a signal received by the signaling means to a predetermined scale to instruct a subject whether he should or should not ingest said dosage form. The predetermined scale may be in the form of a written scale provided with the medicament and/or stored on a website and/or cloud computing, the latter such that it may be accessed by the subject or user via the use of any personal computer or even directly by a scanner and/or receiver (as described above) that the subject may use to capture the signal from the signaling means (the latter especially when a passive micro-electronic system is used as signaling means).

The signal may be a visual signal, preferably a color signal, and the signaling means may be in the form of indicia capable of changing color when the medicament is no longer safe to be ingested and preferably the scale indicates what the visual signal stands for. In this case, the subject or user may manually compare the visual signal received by the signaling means to the predetermined scale and assesses its meaning. For example, if the visual signal received and/or read by the subject is identical or equal to that represented in the predetermined scale as an indication that the dosage form article has been exposed to a temperature above a critical predetermined value, then the subject or user knows that it is not safe to ingest the medicament. It is apparent that the comparison may be done also electronically by scanning the signaling means with a scanning and/or receiving device and allowing it to compare the input signal with the predetermined scale via corresponding processor. It is also apparent that when the signaling means is a passive micro-electronic system, the comparison is achieved electronically via e.g. a processor (as described in the signaling means section above), the subject or user being thus directly informed of the final answer as to safe or not safe to ingest.

Figure 4A:
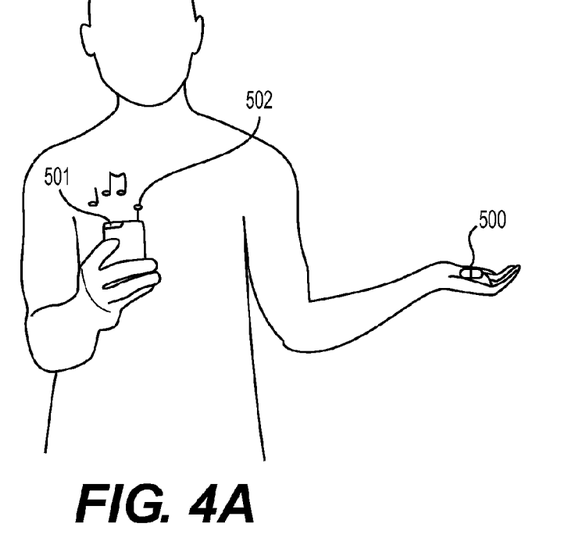
Figure 4B:
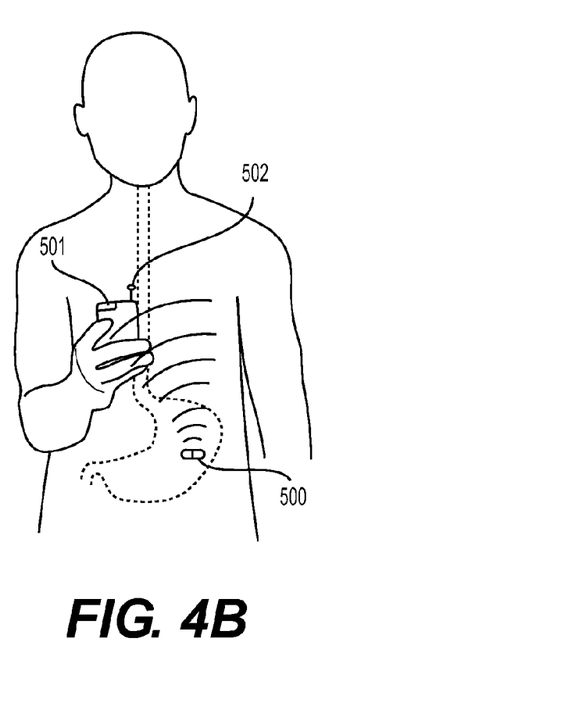

Further or as an alternative to the above method, a method for the automatic prompting of a subject to take a medicament, FIG. 4 showing an exemplary illustration of the method, the method comprising the steps of: providing a portable communication device 501 arranged to provide a warning (FIG. 4A), preferably selected from visual, sound, and combinations thereof, to a subject when it is time to ingest a medicament; providing a dosage form 500 as described herein; providing a receiver 502 capable of detecting a signal generated by the signaling means, the receiver being arranged to provide a further signal to a processing device, the processing device capable of recording said further signal and to instruct the communication device 501 to stop providing said warning (FIG. 4B); and allowing said receiver 502 to detect said signaling means; wherein said warning is de-activated only when the subject places said receiver 502 proximal to said dosage form, and the signaling means stored therein is detected.

Typically the signaling means is detected by the receiver only after the dosage form article is ingested. In these embodiments the signaling means may be arranged to trigger a signal only when the dosage form article is at a predetermined position in the gastrointestinal tract, such that the receiver only detects the signal at this point and only at this point the portable communication device is instructed to stop the warning. This may be achieved by any of the respective arrangements described above, such as via use of a power source generating energy to power a signal burst only when reacting with in-body acids. This has the advantage that the subject is prompted when a given medicament must be taken, the prompting ending only when the signaling means is scanned, detected and/or drug ingested, thus ensuring that the subject strictly keeps to a given medical regimen. This may be particularly important for medications wherein strict compliance (e.g. frequency and time) must be controlled and ensured.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm" (i.e. every value in a practical range close to 40 mm).

The invention claimed is:

1. A dosage form article (100) suitable for oral administration, comprising more than one compartments (101*a*, 101*b*) each delimited by a plurality of distinct segments (102, 103, 104) of the dosage form article (100), said distinct segments being selected from the group consisting of body parts (102, 104), cap parts (103) and combinations thereof, wherein said dosage form article (100) comprises:
   at least one first body part (102) and at least one first cap part (103) each comprising inner (105) and outer (106) surfaces, wherein said first body part (102) is telescopically engageable with said first cap part (102, 103); and
   at least one second body part (104), comprising inner (105) and outer (106) surfaces, being telescopically engageable with said at least one first body (102) or cap (103) parts or both,
characterized in that at least one of the second body parts (104) is arranged within said at least one first body part (102) or cap part (103) or both such that a distinct first compartment (101*a*) is formed between the outer surface (106) of said second body part (104) and the inner surface (105) of said first body part (102) or cap part (103) or both.

2. A dosage form article (100) according to claim 1 wherein the at least one of the second body parts (104) is arranged within the first body part (102) such that, once the first cap part (103) is telescopically connected with the first body part (102), second body part (104) or both, the second body part (104) separates a volume formed by the first body and cap parts (103), (103) into at least two distinct compartments.

3. A dosage form article (100) according to claim 1 wherein the first body part (102) is arranged to telescopically engage with the first cap part (103) such that at least a portion of the inner surface (105) of the first cap part (103) abuts at least a portion of the outer surface (106) of the first body part (102), and wherein the at least second body part (104) is arranged to telescopically engage with the first body part (102) such that at least a portion of the inner surface (105) of the first body part (102) abuts at least a portion of the outer surface (106) of the second body part (104).

4. A dosage form article (100) according to claim 1 wherein the second body part (104) is arranged such that a second compartment (101*b*) is formed between the inner surface (105) of at least one of the second body parts (104) and the inner surface (105) of the first cap part (103).

5. A dosage form article (100) according to claim 1 wherein each body and cap parts (102, 103, 104) comprise an open end (201) and a closed end (202), wherein the first and at least second body parts (102, 104) comprise a first area (A1, A1') proximal to the open end (201) and a second area (A2, A2') proximal to the closed end (202) and distal from said open end (201), wherein the area ratio (A1/A2) of the first body part (102) is less than the area ratio (A1'/A2') of the second body part (104).

6. A dosage form article (100) according to claim 4 wherein the area ratio (A1'/A2') of the second body part (104) is at least 1.1 times greater than the area ratio (A1/A2) of the first body part (102).

7. A dosage form article (100) according to claim 1 wherein each body and cap parts (102, 103, 104) comprise one or more protruding locking means (107) and/or one or more recessed locking means (108), the protruding locking means (107) capable of mechanically engaging with the recessed locking means (108) to provide a locking force joining the body, cap parts (102, 103, 104) and/or combinations thereof, together.

8. A dosage form article (100) according to claim 7 wherein the at least first and second body parts (102, 104) each comprise one or more protruding locking means (107) arranged in series with one or more recessed locking means (108) along an axis perpendicular to the Y-axis.

9. A dosage form article (100) according to claim 1 wherein at least a first compartment (101*a*) is delimited by the first body part (102) and one of the at least second body parts (104), and wherein at least a second compartment (101*b*) is delimited by the first cap part (103) and one of the at least one second body parts (104).

10. A dosage form article (100) according to claim 1 comprising one or more further second body parts each arranged within at least one second body part such that at least one further compartment is formed between an outer surface of the further second body part and the inner surface of the at least one second body part (104).

11. A dosage form article (100) according to claim 1 wherein the first compartment (101*a*) comprises a first drug or a signaling means therein and another of the compartments comprises a second drug therein.

12. A dosage form article (100) according to claim 10 wherein the first and second drugs are in solid or liquid form.

13. A dosage form article (100) according to claim 1 wherein the first body part (102) is translucent such that the second body part (104) and/or the first compartment (101*a*) can be seen through the dosage form article.

14. A dosage form article (100) according to claim 1 wherein a liquid seal is comprised between the outer surface (106) of the second body part (104) and the inner surface (105) of the first body part and/or between the outer surface (106) of the first body part (102) and the inner surface (105) of the first cap part (103).

15. A method of filling a dosage form article (100) according to claim 1, said method comprising:
   providing a first body part (102);
   filling said first body part (102) with a first medium;
   inserting a second body part (104) into said first body part (102) such that a first compartment (101*a*) is formed for storing said first medium and optionally joining said second body part (104) to said first body part (102);
   filling said second body part (104) with a second medium;
   optionally, connecting a first cap part (103) with said first body part (102) or second body part (104) or both, such that a second compartment (101*b*) is formed for storing said second medium; and optionally, wherein the first medium is selected from a drug in solid or liquid state, or a signaling means, and the second medium is selected from a drug in solid or liquid state.

16. A dosage form article (100) according to claim 5, wherein the open end is the only open end such that a semi-enclosed volume substantially tubular in shape is formed.

17. A dosage form article (100) according to claim 7, wherein the protruding locking means (107) is in the form of a locking ring protruding along a plane perpendicular to a Y-axis in a direction from the outer surface (106) to the inner surface (105) and the recessed locking means (108) is in the form of a recessed ring, the recess starting from the outer surface (106) and extending towards the inner surface (105).

18. A dosage form article (100) according to claim 9, wherein:
   (i) the first compartment (101*a*) is delimited by the inner surface (105) of the first body part (102) and the outer surface (106) of the second body part (104);
   (ii) the second compartment (101*b*) is delimited by the inner surface (105) of the first cap part (103) and the inner surface (105) of the second body part (104); or
   (iii) both (i) and (ii).

19. A dosage form article (100) according to claim 12, wherein the first and second drugs are in different phases.

20. A dosage form article (100) according to claim 14, wherein the liquid seal is formed by allowing a sealing liquid to enter a spacing between said outer and inner surfaces (106, 105) followed by drying.

* * * * *